(12) United States Patent
Holmes et al.

(10) Patent No.: US 8,609,139 B2
(45) Date of Patent: Dec. 17, 2013

(54) FORMULATIONS FOR ENHANCED BIOAVAILABILITY OF ORALLY ADMINISTERED POLAR AGENTS

(75) Inventors: Eric Holmes, Bothell, WA (US); Michael Hite, Seattle, WA (US)

(73) Assignee: Ala Wai Pharma, Inc., Palo Alto, CA (US)

( * ) Notice: Subject to any disclaimer, the term of this patent is extended or adjusted under 35 U.S.C. 154(b) by 299 days.

(21) Appl. No.: 12/741,141

(22) PCT Filed: Nov. 5, 2008

(86) PCT No.: PCT/US2008/082463
§ 371 (c)(1),
(2), (4) Date: May 6, 2011

(87) PCT Pub. No.: WO2009/061805
PCT Pub. Date: May 14, 2009

(65) Prior Publication Data
US 2011/0206764 A1 Aug. 25, 2011

Related U.S. Application Data

(60) Provisional application No. 61/001,874, filed on Nov. 5, 2007, provisional application No. 61/030,056, filed on Feb. 20, 2008.

(51) Int. Cl.
*A61K 9/48* (2006.01)

(52) U.S. Cl.
USPC ...................................................... 424/463

(58) Field of Classification Search
None
See application file for complete search history.

(56) References Cited

U.S. PATENT DOCUMENTS

| 7,208,176 B2 | 4/2007 | Faour et al. | |
|---|---|---|---|
| 2002/0155154 A1 * | 10/2002 | Wong et al. | 424/456 |
| 2004/0062801 A1 * | 4/2004 | Faour et al. | 424/468 |

OTHER PUBLICATIONS

Artursson et al, Caco-2 Monolayers in Experimental and Theoretical Predictions of Drug Transport, Adv Drug Deliv Rev., 2001, 46(1-3):27-43.
Aungst et al, Enhancement of the intestinal absorption of peptides and non-peptides, Journal of Controlled Release, 1996, 41:19-31.
Constantinides, Lipid microemulsions for improving drug dissolution and oral absorption: physical and biopharmaceutical aspects, Pharm Res, 1995, 12(11):1561-1572.
International Search Report and the Written Opinion dated Jan. 8, 2009 for PCT Application No. PCT/US2008/82463.
Shah et al, Modulation of ganciclovir intestinal absorption in presence of absorption enhancers, Pharm Sci, 2007, 96:2710-2722.
Shah et al, Role of Caco-2 Cell Monolayers in Prediction of Intestinal Drug Absorption, Biotechnol Prog., Jan.-Feb. 2006, 22(1):186-98.
Wiebe et al, Glycerol disrupts tight junction-associated actin microfilaments, occluding, and microtubules in Sertoli cells, J. Androl, 2000, 21:625-635.
Office Action dated Nov. 15, 2011 for China Application No. 200880123793.9.

* cited by examiner

*Primary Examiner* — Brian Gulledge
*Assistant Examiner* — Snigdha Maewall
(74) *Attorney, Agent, or Firm* — Kilpatrick Townsend & Stockton LLP

(57) ABSTRACT

A composition is described having improved oral permeability of polar agents such as neuraminidase inhibitors. The composition includes one or more polar agents and one or more permeability enhancers such that the composition increases the amount of the polar agent capable of being transported across a Caco-2 cell membrane by at least 150% relative to the amount capable of being transported across the Caco-2 Cell membrane in the absence of the permeability enhancer. Oral dosage forms including the composition, and methods of treating or preventing influenza infection are also provided.

15 Claims, 5 Drawing Sheets

FORMULATIONS FOR ENHANCED BIOAVAILABILITY OF ORALLY ADMINISTERED POLAR AGENTS

CROSS REFERENCE TO RELATED APPLICATIONS

This application claims the benefit of U.S. Provisional Application Nos. 61/001,874 filed Nov. 5, 2007, and 61/030,056 filed Feb. 20, 2008. The contents of each of these applications is incorporated by reference herein, in their entirety and for all purposes.

FIELD OF THE INVENTION

The invention relates generally to enhancing the permeability and bioavailability of active agents. More specifically, the invention relates to enhancing the permeability and bioavailability of polar active agents.

BACKGROUND OF THE INVENTION

Peramivir is a member of a class of antiviral agents that work by inhibiting viral neuraminidase, an enzyme essential for the influenza virus to replicate and infect its hosts. In addition to influenza A and B, avian influenza virus (H5N1) has been shown to be sensitive to peramivir. More specifically, depending on the influenza strain, peramivir has been determined to be 2 to 10 times more potent as a neuraminidase inhibitor than oseltamivir (Tamiflu®) and zanimivir, based on experimentally determined concentrations of each required for 50% inhibition of neuraminidase activity in vitro.

It has been reported that studies in rodents and primates have established the safety and efficacy of intramuscular injection of peramivir in a mouse influenza model. Further intravenous and intramuscular formulations of peramivir are reported to have been evaluated in pre-clinical animal models with success. However, human studies with oral forms of peramivir have demonstrated very poor oral bioavailability of peramivir. In particular it has been reported that in a phase III clinical trial of an oral formulation of peramivir, the antiviral activity against influenza A and B did not reach statistical significance.

Accordingly there is a need for neuraminidase inhibitor compositions which exhibit improved bioavailability and efficacy when administered orally for treatment or prevention of influenza infections.

SUMMARY OF THE INVENTION

The invention features compositions comprising at least one polar agent and at least one permeability enhancer. The compositions can increase the amount of a polar agent capable of being transported across a cell membrane such as a Caco-2 cell membrane, and can increase this amount by at least 150% relative to the amount capable of being transported across the cell membrane in the absence of the permeability enhancer. Suitable permeability enhancers for use in the inventive compositions can be fatty acids, fatty acid esters, fatty acid salts, glycerol, glycerol monocaprylate, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2-alkoxypropyl-phosphocholine derivatives, dimethylpalmityl-ammonio propanesulfonate, alkanoylcholines, N-acetylated amino acids, mucoadhesive polymers, phospholipids, piperine, 1-methylpiperazine, α-amino acids, or mineral oil. Any polar agent that is poorly absorbed by cells can be used in the inventive compositions. In some preferred aspects, the agent is a neuraminidase inhibitor such as oseltamivir, zanamivir, or peramivir. The invention also provides oral dosage forms of the compositions, which comprise a therapeutically effective amount of the polar agent and a permeability-enhancing amount of a permeability enhancer. The oral dosage forms can further comprise an enteric- or pH-sensitive coating or layer surrounding the composition. In the oral dosage forms, the permeability enhancer can be glycerol, glycerol monocaprylate or dimethylpalmityl-ammonio propanesulfonate. And, the polar agent can be a neuraminidase inhibitor such as oseltamivir, zanamivir, or peramivir. The permeability enhancer can be present in the composition at a concentration from about 5% to about 95% of the combined weight of the polar agent and the permeability enhancer.

Also featured are methods for treating or preventing influenza infection. Generally, the methods comprise administering to a subject in need thereof a composition comprising at least one neuraminidase inhibitor and at least one permeability enhancer, including oral dosage forms of such compositions. In the compositions used in the methods, the permeability enhancer can be glycerol, glycerol monocaprylate or dimethylpalmityl-ammonio propanesulfonate, among others, and the neuraminidase inhibitor can be oseltamivir, zanamivir, or peramivir, among others.

DETAILED DESCRIPTION OF THE INVENTION

Figure 1:
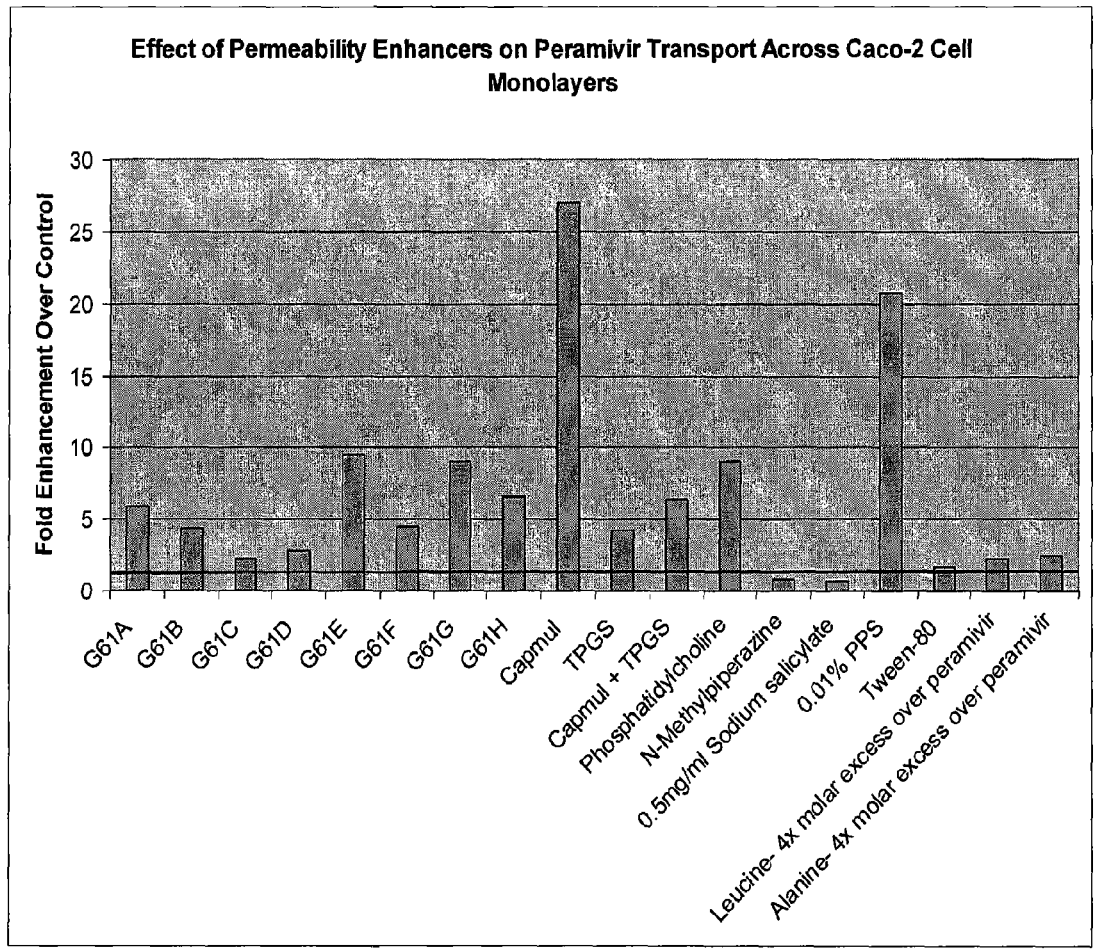
FIG. 1 shows the effect of permeability enhancers on peramivir transport across Caco-2 cell monolayers. Caco-2 cell permeability assays were conducted according to standard procedures using monolayers having a minimum transepithelial electrical resistance (TEER) of >200 Ωcm2. Except as is indicated each enhancer was present at 1% final concentration (w/w) in HBSS. The fold enhancement in transport rate over control (peramivir in HBSS alone) provided by each enhancer is shown. The line indicates a ratio of 1:1 (no enhancement).
Figure 2:
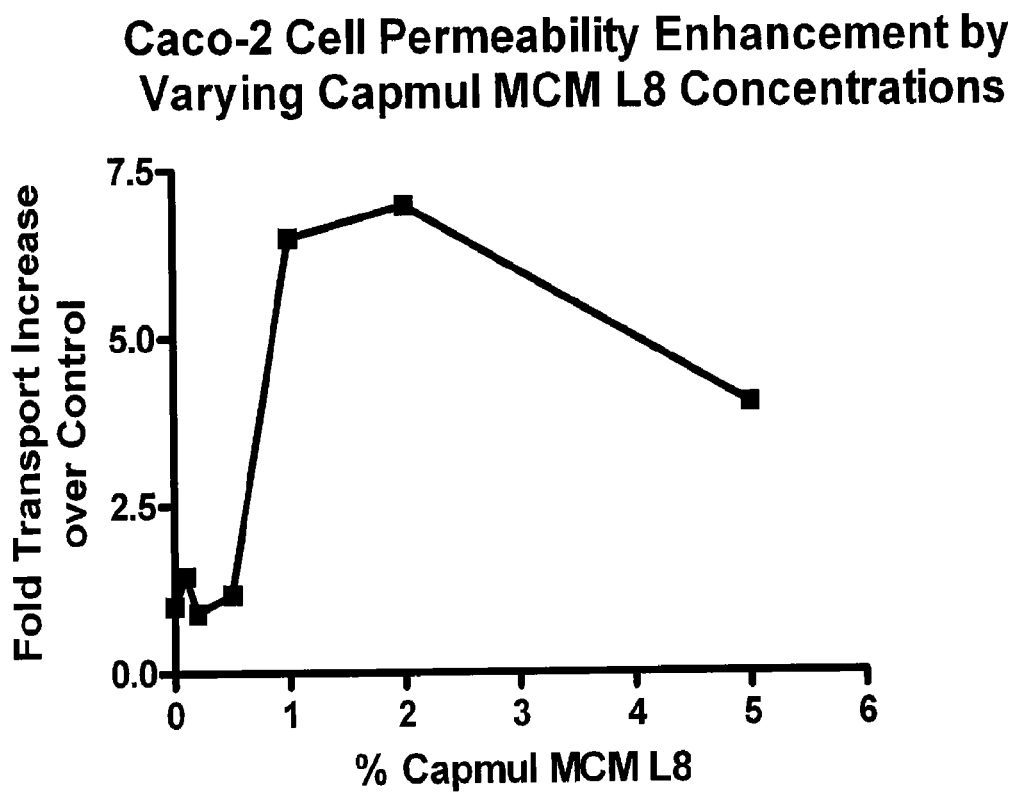
FIG. 2 shows the effect of increasing Capmul MCM L8 concentrations on permeability enhancement of peramivir across Caco-2 cell monolayers. Enhancement saturates at about 1-2% Capmul MCM L8 and declines at higher concentration. The experiment-to-experiment variation of the maximum fold-enhancement at 1% Capmul MCM L8 shown here and in FIG. 1 is believed to be attributed to differences in negative control permeability (HBSS alone) between the experiments.
Figure 3:
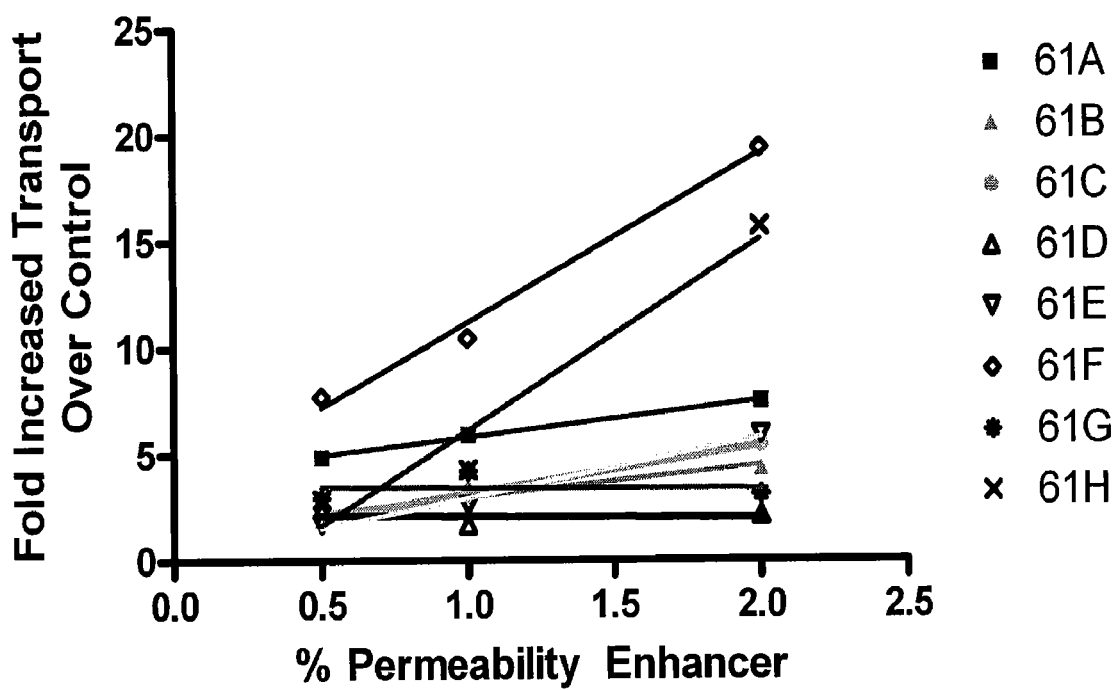
FIG. 3 shows the effect of increasing Gattefosse compositions on permeability enhancement of peramivir across Caco-2 cell monolayers. In contrast to results using Capmul MCM L8, enhancement increases are linear up to at least 2% final concentration, suggesting the maximum potential enhancement occurs at much higher concentrations.
Figure 4:
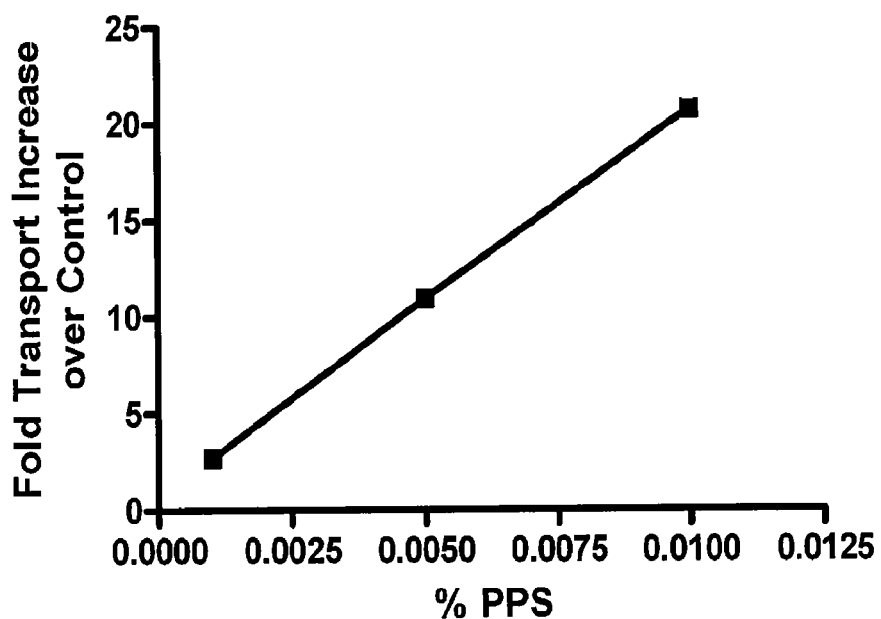
FIG. 4 shows the effect of increasing PPS concentrations on permeability enhancement of peramivir across Caco-2 cell monolayers. A substantial linear increase in peramivir permeability is observed as the PPS concentration is increased from 0.001% to 0.01% final concentration.
Figure 5:
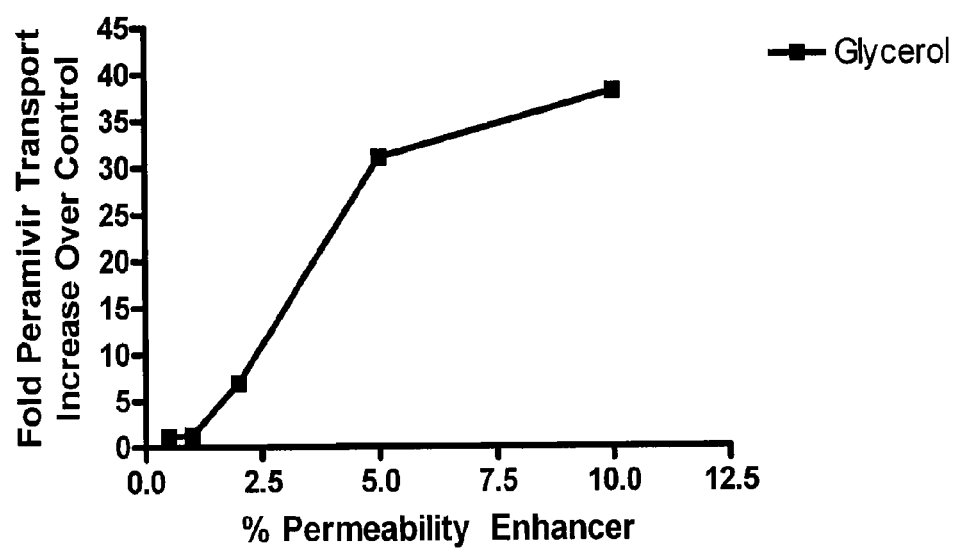
FIG. 5 shows the effect of increasing glycerol concentrations on permeability enhancement of peramivir across Caco-2 cell monolayers. A substantial increase in peramivir permeability is observed as the glycerol concentration is increased from 2% to 5% final concentration.

Peramivir refers to the compound (1S,2S,3S,4R)-3-[(1S)-1-Acetamido-2-ethyl-butyl]-4-(diaminomethylideneamino)-2-hydroxy-cyclopentane-1-carboxylic acid, and has the chemical structure shown below:

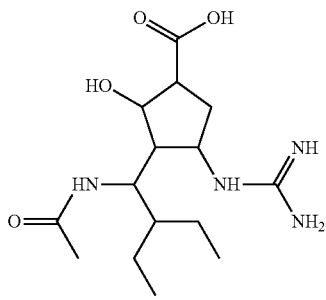 [SMILES: CCC(CC)C(NC(C)=O)C1C(NC(=N)N)CC(C(=O)O)C1O]

Of particular significance is the presence of three functional groups: an alcohol —OH group, a carboxylic acid group, and a guanidino group. The guanidino group is considered likely to be a major contributor to the improved activity of peramivir over other agents having neuraminidase activity. Yet, the poor oral absorption of peramivir and alkyl esters thereof may be due in large part to the highly polar nature of the guanidino group, particularly when in the protonated form such as is found in the zwitterionic form of peramivir. Without intending to be limited to any particular theory or mechanism of action, it is believed that one or more polar groups on the agent limit permeability of the compound, and this is particularly problematic where the polar agent is not or is only weakly transported across the cell membrane by a transport protein. It has now been found that inclusion of one or more permeability enhancer compounds in formulations with highly polar agents that are poorly absorbed, and in particular, neuraminidase inhibitor formulations, can increase the amount of agent that is absorbed by cells, and ultimately increase the bioavailability to the organism. In particular, permeability enhancer compound(s) are believed to provide polar agents such as neuraminidase inhibitors with improved oral efficacy with respect to absorption across cellular membranes. Without wishing to be bound by any particular theory or mechanism of action, it is believed that a permeability enhancer compound may facilitate increased absorption of highly polar compounds such as neuraminidase inhibitors through cellular tight junctions, may act to promote absorption through a transcellular pathway, or may act to increase permeability through other mechanisms. Accordingly, the invention provides a composition and method for improving oral bioavailability and activity of polar compounds such as neuraminidase inhibitors.

"Polar" compounds/agents are those that have at least one group that confers a degree of partial or permanent charge on the compound that is greater than or equal to the charge of a hydroxyl group, more preferably greater than or equal to the charge of a carboxyl group, more preferably greater than or equal to the charge of an imidazole group, more preferably greater than or equal to the charge of an amino group, and more preferably greater than or equal to the charge of a guanidino group, phosphate, or sulfate group.

With respect to a composition aspect of this invention, there is provided a composition comprising at least one polar agent and a permeability enhancer, wherein the composition provides a Caco-2 polar agent permeability at least 150% of the permeability observed in compositions that do not have a permeability enhancer. As will become apparent from the following disclosure and examples, an enhancement in permeability of 150% is also the equivalent of a 1.5-fold improvement in polar agent permeability. In preferred aspects, the polar agent is a neuraminidase inhibitor.

Any neuraminidase inhibitor known or discovered in the art can be used in accordance with the inventive formulations and methods. Non-limiting examples of such agents include cis-3-[(methylcarbonylamino)methyl]cyclopentanecarboxylic acid; trans-3-amino-c-.sup.4-(methylcarbonylamino)methyl-r-cyclopentanecarboxylic acid; trans-3-{[(amino)(imino)methyl]amino}-c-4-[(methylcarbonylamino)methyl]cyclopentan-r-carboxylic acid; 4(3-{[(amino)(imino)methyl]amino}-3.alpha.-[(2-hydroxy-1-methylcarbonyl-amino)ethyl]-1-cyclopentanecarboxylic acid; sodium 3.beta.-{[amino)(imino)methyl]amino}-4.alpha.-[(2-hydroxy)(1-methylcarbonylamino)ethyl]cyclopentan-r-carboxylate; trans-3-amino-trans-1-hydroxy-cis-4[(hydroxymethyl)(methylcarbonylamino)methyl]cyclopentan-r-carboxylic acid; trans-3-{[(amino)(imino)methyl]amino}-trans-1-hydroxy-cis-4-[(2-hydroxymethyl)(1-methylcarbonylamino)ethyl]cyclopentan-r-carboxylic acid; 3.beta.-amino-4.alpha.-[(1-methylcarbonylamino)(2,3,4-trihydroxy)butyl]cycl opentancarboxylic acid; 3.beta.-{[(amino)(imino)methyl]amino}-4.alpha.-[(1-methylcarbonylamino)(2,3,4-trihydroxy)butyl]-cyclopentancarboxylic acid; cis-3-{[(amino)(imino)methyl]amino)-trans-1-hydroxy-trans-4-[(1-methylcarbonylamino)(2-trifluoromethyl-carbonyloxy)ethyl]cyclopentan-r-carboxylic acid; t-3-amino-c-4-[(1-methylcarbonylamino)(2-phenylmethoxy)ethyl]-t-1-hydroxycyclopentan-r-carboxylic acid; c-3-{[(amino(imino)methyl]amino}-t-1-hydroxy-t-4-{(methylcarbonylamino)([(methyl)-(methoxy)amino]carbonyl}methyl}cyclopentan-r-carboxylic acid; 3.beta.-{[(amino)(imino)methyl]amino}-4.alpha.-{{4-[(methoxy)(methyl)amino]1-(methylcarbonylamino-2-oxo}butyl}cyclopentancarboxylic acid; t-3-{[(amino)(imino)methyl]amino}-c-4-[(diethylaminocarbonyl)(methylcarbonylamino)methyl]-t-1-hydroxycyclopentan-r-carboxylic acid; t-3-amino-c-4-[(di-n-propylaminocarbonyl)(methylcarbonylamino)methyl]-t-1-hydroxy-cyclopentan-r-carboxylic acid; t-3-{[(amino)(imino)methyl]amino}-c-4-[di-n-propylaminocarbonyl)(methylcarbonylamino)methyl]-t-hydroxycyclopentan-r-carboxylic acid; c-3-{[(amino)(imino)methyl]amino}-t-4-[(di-n-propylaminocarbonyl)(methylcarbonylamino)methyl]-t-1-hydroxycyclopentan-r-carboxylic acid; 3.beta.-{[(amino)(imino)methyl]amino}-4.alpha.-[(di-n-propylaminocarbonyl)(methylcarbonylamino)-methyl)cyclopentancarboxylic acid; 3.beta.-{[(amino)(imino)methyl]amino}-4.alpha.-[(methylcarbonylamino)(3-pentylaminocarbonyl)methyl]cyclopentancarboxylic acid; 3.beta.-{[Amino)(imino)methyl]amino}-4.alpha.-[(diethylaminocarbonyl)(methylcarbonylamino)methyl]cyclopentancarboxylic acid; 3.beta.-{1[(Amino)(imino)methyl]amino}-4.alpha.-{[(ethyl)(propyl)aminocarbonyl](methylcarbonylamino)methyl}cyclopentancarboxylic acid; 3.beta.-{([(Amino)(imino)methyl]amino}-4.alpha.-{[(ethyl)(propyl)aminocarbonyl]methyl-carbonylamino)methyl}cyclopentancarboxylic acid; 3.beta.-{[(Amino)(imino)methyl]amino}-4.alpha.-[1-(1-methylcarbonylamino)pent-2-enyl]cyclopentancarboxylic acid; 3.beta.-{[(Amino)(imino)methyl]amino}-4.alpha.-[1-(-methylcarbonylamino)pentyl]cyclopentancarboxylic acid; Phenylguanidine; 1-Phenylbiguanide; 4-Acetylaminobenzoic acid; 2-Acetylaminobenzenesulfonic acid; 4-Acetylaminophenylphosphoric acid; 4-(Trifluoroacetamido)benzoic acid; 4-Thioacetamidobenzoic acid; 4-[(Methylsulfonyl) amino]benzoic acid; 3-Guanidinobenzoic acid; 3-[Amino (cyanoimino)methyl]aminobenzoic acid; 3-Cyanoaminobenzoic acid; 3-(2-Amino-2-imino)ethylbenzoic acid; 4-(Acetamino)phenylacetic acid; 4-(Methylaminocarbonyl) benzoic acid; 4-Acetylamino-3-hydroxymethylbenzoic acid; beta.-(2-N-Acetylamino-5-carboxyphenyl)ethanol; 4-Acetylamino-3-(2',3'-dihydroxypropyl)benzoic acid; 4-Acetylamino-3-aminobenzoic acid; 4-Acetylamino-3-[(aminoiminomethyl)amino]benzoic acid; 3-[(Aminoiminomethyl) amino]-4-(2-methylpropionylamino)benzoic acid; 4-Acetylamino-3-[(hydroxylimino)methyl]benzoic acid; 3-[(Aminoiminomethyl)amino]-4-[(methylsulfonyl)amino] benzoic acid; 3-[(N-Hydroxyimino)methyl]-4-[(methylsulfonyl)amino]benzoic acid; 3-[((Aminoimino)methyl) amino]-4-methoxybenzoic acid; 3-[(Aminoiminomethyl) amino]-4-hydroxybenzoic acid; 3,5-Bis-[(aminoiminomethyl)amino]benzoic acid; 3-Amino-5-{[(aminoimino)methyl]amino}benzoic acid; 3-[(Aminoiminomethyl)amino]-5-[(N-hydroxylimino)methyl]benzoic acid; and 3-[(Aminoiminomethyl)amino-5-hydroxymethyl)-4-(methylsulfonyl)aminobenzoic acid. Highly preferred neuraminidase inhibitors are (3R,4R,5S)-4-acetylamino-5-amino-3-(1-ethylpropoxy)-1-cyclohexene-1-carboxylic acid ethyl ester (oseltamivir), 5-acetamido-4-guanidino-6-(1,2,3-trihydroxypropyl)-5,6-dihydro-4H-pyran-2-carboxylic acid (zanamivir), and (1S,2S,3S,4R)-3-[(1S)-1-Acetamido-2-ethyl-butyl]-4-(diaminomethylideneamino)-2-hydroxy-cyclopentane-1-carboxylic acid (peramivir).

The composition of this invention also contemplates an oral composition comprising a therapeutically effective amount of at least one polar agent and a permeability-enhancing amount of a permeability enhancer. In this aspect, the enhancing amount of permeability enhancer compound is an amount or concentration which produces a Caco-2 polar agent permeability at least 150% of (i.e., 1.5-fold over) that provided by the polar agent in the absence of a permeability enhancer. In some preferred aspects, the polar agent is a neuraminidase inhibitor.

The invention also provides a method for improving the oral bioavailability of polar agents that are not absorbed or only weakly absorbed through a cell membrane. Generally, such methods comprise providing a pharmaceutical formulation comprising a therapeutically effective amount of at least one polar agent and a permeability-enhancing amount of one or more suitable permeability enhancer compounds in a pharmaceutical formulation or dosage form thereof which is suitable for oral administration. Examples of suitable forms include, for example, capsules, tablets, caplets, various sustained or controlled release dosage forms, solutions, suspensions, and the like, each of which may include acceptable pharmaceutical excipients which are well known to those skilled in the art and suitable for formulation of the dosage form in question. In some preferred aspects, the polar agent is a neuraminidase inhibitor.

As used herein, the term "permeability enhancer," "enhancer" and variations thereof refer to compounds which improve the bioavailability of polar agents when incorporated into oral formulations. A neuraminidase inhibitor permeability enhancer may be defined as a compound capable of increasing the rate of neuraminidase inhibitor transport across a Caco-2 cell membrane by 1.5-fold (150%) or more compared to the neuraminidase inhibitor transport rate in the absence of the enhancer compound. Any means known or otherwise available to those of skill in the art can be used to determine the transport rate, including those Caco-2 cell permeability assays described and exemplified herein.

With respect to the bioavailability of the polar agents, the presence of a permeability enhancer increases the bioavailability of the agent to the subject relative to the bioavailability of the agent in the absence of the permeability enhancer. Thus, in some aspects, the presence of the permeability enhancer increases bioavailability of the agent about 1.5 times the amount of bioavailability of the agent in the absence of the permeability enhancer, More preferably, the presence of the permeability enhancer increases bioavailability of the agent by about 2 times, more preferably about 2.5 times, more preferably about 3 times, more preferably about 3.5 times, more preferably about 4 times, more preferably about 4.5 times, more preferably about 5 times, more preferably about 6 times, more preferably about 7 times, more preferably about 8 times, more preferably about 9 times, more preferably about 10 times, more preferably about 12 times, more preferably about 15 times, more preferably about 17 times, more preferably about 20 times, more preferably about 22 times, more preferably about 25 times, more preferably about 27 times, more preferably about 30 times or even greater times the amount of bioavailability of the agent in the absence of the permeability enhancer.

The invention contemplates that highly polar agents that have low bioavailability in the absence of a permeability enhancer will have enhanced bioavailability when combined with a permeability enhancer in a formulation. It is desirable that the bioavailability of the agent be enhanced to at least about 10% in the subject to which the agent is administered, more preferably at least about 15%, more preferably at least about 20%, more preferably at least about 25%, more preferably at least about 30%, more preferably at least about 35%, more preferably at least about 40%, more preferably at least about 45%, more preferably at least about 50%, more preferably at least about 55%, more preferably at least about 60%, more preferably at least about 65%, more preferably at least about 70%, and more preferably at least about 75% or more in the subject to which the agent is administered, when formulated with a permeability enhancer.

A variety of classes of compounds may serve as suitable permeability enhancers according to the invention. A first category includes fatty acids and salts and esters thereof, including mono-, di-, and triglycerides. Medium chain length fatty acids, especially C8 and C10 acids, and their salts and esters are particularly useful. Suitable specific examples include sodium caprylate, sodium caprate, CAPMUL® glycerides (available from Abitec of Columbus, Ohio), LABRASOL® glycerides (PEG-8 caprylic/capric glycerides, available from Gattefossé SAS of Saint Priest, Cedex, France), GELUCIRE® 44/14 (PEG-32 glyceryl laurate EP, available from Gattefossé), other glycerides & fatty acid esters, CREMOPHOR® (BASF, Ludwigshafen, Germany), D-α-tocopheryl polyethylene glycol 1000 succinate, vegetable oils, polyoxyiglycerides, and medium chain mono- and diacylglycerides.

One example of this class, CAPMUL® MCM L8 (glycerol monocaprylate) (available from Abitec of Columbus, Ohio), is composed of mono- and diglycerides of medium chain fatty acids (mainly caprylic, with some capric) and 7% maximum free glycerol. It contains at least 44% alpha monoglycerides (as caprylate).

Other examples of this class of enhancers include GATTEFOSSÉ compositions 61A through 61H which are proprietary to Gattefossé SAS, but generally are composed of mixtures containing one or more of medium chain mono-, di-, or triglycerides, polysorbate derivatives, polyoxyl castor oil derivatives, polyethylene glycol derivatives including polyethylene glycol glycerides, polyoxyl ethers, vegetable oils, and similar GRAS (generally regarded as safe) lipidic components in varying amounts. These components are part of individual commercial products such as CAPRYOL™ 90, CAPRYOL™ PGMC, LAUROGLYCOL™ 90, GELUCIRE® 44/14, Plurol Oleique CC497, LABRASOL®, LABRAFIL® M1944CS (apricot kernel oil PEG-6 esters), Transcutol HP, Peceol, and Maisine 35-1, all of which are available from Gattefossé SAS.

While not falling directly within this class, glycerol itself has been found to impart excellent permeability enhancement, particularly for neuraminidase inhibitors. This result was not anticipated as glycerol is not considered a permeability enhancer.

A second category of enhancers includes surfactants having a steroidal structure, such as bile acid salts. Examples of suitable compounds include sodium cholate, sodium deoxycholate, glycocholate, glycoursodeoxycholate, taurocholate, taurodeoxycholate, and steroid detergents/bile salts. Other surfactants may also be suitable permeability enhancers, including cationic, anionic, and nonionic surfactants. Examples include polysorbate 80, hexadecyldimethylbenzylammonium chloride, N-hexadecylpyridinium bromide, dodecyltrimethylammonium bromide, hexadecyltrimethylammonium bromide, tetradecyl-β-D-maltoside, octylglucoside, glycyrrhetinic acid, 3-(N,N-dimethylpalmitylammonio)propane-sulfonate, and sodium lauryl sulfate.

Cyclodextrins may also be used as suitable enhancers. Examples include β-cyclodextrin, hydroxypropyl-β-cyclodextrin, γ-cyclodextrin, and hydroxypropyl-γ-cyclodextrin.

A variety of other compounds may also be used as enhancers. Examples include sodium salicylate, ethylenediamine tetraacetic acid (EDTA), citric acid, chitosan & chitosan derivatives, N-trimethyl chitosan chloride, monocarboxymethyl-chitosan, palmitoyl carnitine chloride, acyl carnitines, ethylene glycol tetraacetic acid (EGTA), 3-alkylamido-2-alkoxypropyl-phosphocholine derivatives, alkanoylcholines, N-acetylated amino acids (based on α- and non-α-amino acids), mucoadhesive polymers, phospholipids, piperine, 1-methylpiperazine, α-amino acids, and mineral oil.

Thus a wide variety of enhancer compounds may be selected from the group consisting of fatty acids, fatty acid esters, fatty acid salts, glycerol, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2-alkoxypropyl-phosphocholine derivatives, alkanoylcholines, N-acetylated amino acids, mucoadhesive polymers, phospholipids, piperine, 1-methylpiperazine, α-amino acids, and mineral oil.

The above examples of permeability enhancers are exemplary only and do not constitute a complete list of potential permeability enhancers. Any compound capable of increasing the oral absorption of a neuraminidase inhibitor by at least 50% is considered to be within the scope of this invention.

The permeability enhancer and the polar agent may be mixed in any proportion so long as there is provided a therapeutically effective amount of the polar agent and a permeability-enhancing amount of the enhancer compound. Enhancement in bioavailability of orally administered polar agents can depend on the nature and concentration of the enhancer compound with which the agent is formulated. It is thus contemplated that the required therapeutic amount may be contained in a single dosage form or divided between one or more dosages intended for ingestion at the same time or in sequence.

The permeability enhancers act relatively independently of the concentration of polar agent. Differing permeability enhancers can reach either optimal or maximum enhancement over a wide concentration range depending on their particular inherent enhancement potential. Often, enhancers have a non-linear dose response relationship between concentration of enhancer present and amount of increased polar agent absorption. The amount of enhancer to be utilized in an oral dosage form with a polar agent is initially based upon the enhancement properties observed in Caco-2 cell assays at varying fixed enhancer concentrations. Based upon those results, an effective in vivo amount of enhancer compound for a human formulation can be estimated, demonstrated and optimized without undue experimentation using methods well known to those skilled in the formulation art, to achieve a desired pharmacokinetic in vivo profile.

In formulating the composition of this invention, it will be apparent to those skilled in the formulation art that more effective enhancer compounds would require less polar agent than less effective permeability enhancers to achieve a target pharmacokinetic profile.

Given those considerations and variations, the amount of enhancer may be at least about 0.1 wt % of the combined weight of enhancer and polar agent, more preferably at least about 50 wt %, and more preferably at least 70 wt % of the combined weight of enhancer and polar agent. The amount is preferably at most 95 wt %, more preferably at most 80 wt %, and more preferably at most 75 wt % of the combined weight of the enhancer and polar agent. Thus, as shown in the examples, a typical dosage form may contain a wide range of concentrations of enhancer compounds depending on the compound itself and its efficacy in enhancing the permeability of polar agents following oral administration. Concentrations as low as 0.001% by weight up to 20% have been demonstrated to be effective in enhancement of the permeability of polar agents.

Suitable excipients are well known to those skilled in the formulation art, and any excipient or combination of excipients known in the pharmaceutical art may be used. Examples may include flow aids, stabilizers, surface active agents, binders, dispersing agents, flavorings, taste masking agents, coatings, release control agents, water, and/or other excipients typically employed for formulation of oral dosage forms.

In some embodiments, the excipient may comprise one or more materials selected from the group consisting of microcrystalline cellulose, dicalcium phosphate, lactose, pre-gelatinized starch, carnauba wax, candelilla wax, silica, and magnesium stearate.

The compositions of this invention may in some aspects be prepared by combining one or more polar agents with suitable amounts of either a single permeability enhancer compound or combinations thereof and optionally with other formulation additives/excipients, mixing thoroughly, and either tableting or filling a suitable hard shell capsule or soft gel capsule with the resulting composition. It has been found that in some cases, sonicating the mixture (i.e., exposure of the neuraminidase inhibitor/enhancer mixture to ultrasonic radiation) may increase the efficacy of the enhancer. Common methods for sonication are known in the art, such as use of a probe or bath sonicator.

It has also been found that in some cases, high-energy blending of the mixture (e.g., exposing the mixture to significant sheer forces) may increase the efficacy of the enhancer.

Common methods for high-energy blending include any known in the art, such as stirrers, rotor-stator devices or colloid mills.

It has also been found that in some cases, homogenization or micronization of the mixture (e.g., exposing the mixture to extreme pressure and stress forces, including but not limited to sheer, turbulence, acceleration and impact forces) may increase the efficacy of the enhancer by forming an emulsion of the agent/enhancer mixture in water. Common methods for micronization include any known in the art, such as use of a high pressure homogenizer. Such micronization techniques may significantly reduce the particle size of the mixture in the formulation, providing particle sizes typically <10 um in size. For example, a CAPMUL® MCM L8/neuraminidase inhibitor mixture may be emulsified in about an equal weight of water. This may be done by repeatedly squirting the mixture through a narrow orifice until an emulsion is formed, or by other emulsion-forming techniques known to those of skill in the art. Although a roughly equal weight of water typically works well, other proportions may also be used according to the invention.

All such methods of sonication, high-energy blending, homogenization and micronization may alter the viscosity of the mixture. It has been found that in some cases, the viscosity of the mixture is significantly increased, sometimes by as much as 50% or more. In some cases, an increase in viscosity may be desirable for improved manufacturability (i.e., improved efficiency of filling solid dosage form vessels such as capsules or soft-gels) or improved content uniformity and decreased variability of the mixture. In some aspects, a significant increase in viscosity may increase the efficacy of the enhancer.

In some aspects, a significant increase in viscosity may indicate a successful endpoint of high-energy mixing, sonication or homogenization. It has also been found that in some cases of homogenization, micronization, sonication or high-energy blending of the mixture, an endothermic reaction may accompany the increase in viscosity. In some embodiments, an endothermic reaction may indicate a successful endpoint of high-energy mixing, sonication or homogenization. One exemplary embodiment that shows this effect is a combination of CAPMUL® MCM L8 with peramivir, which upon sonication under some conditions undergoes an endothermic transition during which the mixture suddenly becomes significantly more opaque and the temperature of the mixture rapidly drops. In some cases, for example, the transition results in a temperature drop of about 10° C. from about 65-75° C.

The resulting compositions are typically viscous liquids or paste-like solids. Additional permeability enhancers or formulation additives can either be added prior to sonication or after sonication of the initial lipid/agent composition.

In some embodiments, a tablet, multiparticulate dosage form, capsule, or granule containing the composition may be coated with an enteric or pH-sensitive layer to facilitate drug composition release in the gastro-intestinal tract distal to the stomach. In some embodiments, the enteric coating or pH-sensitive layer may comprise, but is not limited to, one or more materials selected from the group enteric polymers consisting of cellulose acetate phthalate, cellulose acetate trimellitate, hydroxypropyl methylcellulose acetate succinate, hydroxypropyl methylcellulose is phthalate, and polyvinyl acetate phthalate; and anionic polymers based on methacrylic acid and methacrylic acid esters.

This disclosure contemplates a formulation composition comprising at least one polar agent, a permeability enhancer, and optionally other excipients in a tablet or capsule configuration with optional enteric coating. In some embodiments, such compositions are non-aqueous in that water is excluded as a potential excipient and the only water that is present is that which may be present natively or naturally in the individual formulation components. It is also contemplated that the viscosity of liquid formulations for capsule delivery applications according to the invention will be higher than the viscosity of a 5% aqueous solution of that formulation.

The following examples are provided to describe the invention in greater detail. The examples are intended illustrate, not to limit, the invention.

Example 1

General Experimental Procedures

Permeability enhancers such as CAPMUL® MCM L8, GATTEFOSSÉ 61A through GATTEFOSSÉ 61H compositions, glycerol, 3-(N,N-dimethylpalmitylammonio)propane sulfonate (PPS), Leucine, Alanine, Gelucire 44/14, Tween 20, N-methylpiperazine, and d-alpha-tocopheryl polyethylene glycol 1000 succinate (TPGS) were each mixed with peramivir and vortexed and sonicated. For example, in the case of CAPMUL® MCM L8, the enhancer was mixed with peramivir in amounts such that the weight ratio of enhancer to peramivir was in the range of about 333:1 to about 1333:1, and such that when the mixture was subsequently diluted in HBSS to a level at which peramivir was present at a concentration of 15 μg/mL (0.0015%) the enhancer concentration of the sample was in the range of 0.5% to 2.00%, as shown in the table below. Mixing was conducted by sonication (using either a bath or probe sonicator) which converted the relatively low viscosity liquid mixture to a highly viscous or paste-like composition that is a stable and non-separating.

In like manner, other enhancer compounds were mixed with peramivir in amounts such that the weight ratio of enhancer to peramivir was in the range of about 0.7:1 to about 7000:1, and, similarly, such that when the mixture was subsequently diluted to a level at which peramivir was present at a concentration of 15 μg/mL (0.0015%) the enhancer concentration of the sample was in the range of 0.001% to about 10%, as shown in the table below To evaluate the effectiveness of permeability enhancers, data were obtained to demonstrate the ability of one or more permeability enhancer compound(s) to increase peramivir permeability using Caco-2 cell permeability assays. The assays were performed according to the methods described by Artursson P, Palm K, Luthman K., Caco-2 Monolayers in Experimental and Theoretical Predictions of Drug Transport, *Adv Drug Deliv Rev.* 2001 Mar. 1; 46(1-3):27-43, and by Shah P, Jogani V, Bagchi T, Misra A., Role of Caco-2 Cell Monolayers in Prediction of Intestinal Drug Absorption, *Biotechnol Prog.* 2006 January-February;22(1):186-98. Assays were conducted by seeding approximately 68,000 viable Caco-2 cells in 1.12 cm² Costar Transwell inserts (12-well format, 0.4 micron pore size PET membranes) in Dulbecco's Modified Eagles Medium (high glucose) supplemented with 20% fetal bovine serum, glutamine, pyruvate, non-essential amino acids, epidermal growth factor, ITS (insulin, transferrin, selenium), and penicillin/streptomycin. The cells were incubated for 21-25 days with medium changes every 2-3 days. Transepithelial electrical resistance (TEER) readings were conducted to test the quality of the cell monolayer on the Transwell membrane. The membranes were washed in Hank's Balanced Salt Solution (HBSS, available from Mediatech, Inc., Herndon, Va.) and the resistance across the membrane was measured. Wells having TEER readings of 200 Ωcm² or higher were used in the permeability assays.

Assays were conducted by washing the transwell inserts containing a Caco-2 cell monolayer in HBSS and placing them in 12-well plates with 1.5 ml of HBSS in the lower well. The peramivir containing test formulation was diluted into HBSS to provide a peramivir concentration of 15 µg/mL, and 0.5 ml of the solution was added to the transwell insert. Each formulation was tested in triplicate. The transwell inserts were incubated in a 37° C. incubator with rotation at 50 rpm for 30 minutes. At the end of this period the transwell inserts were placed in a fresh 1.5 ml of HBSS in a new well of the 12-well plate and incubated for an additional 30 minutes. A total of 8 to 10 thirty-minute time points were collected by sequentially moving the transwell inserts to fresh 1.5 ml HBSS in successive wells of the 12-well plates. The amount of peramivir transported into the lower wells was quantitated by LC-MS to define the rate of peramivir transported across the membrane for each test formulation. The reference control was composed of peramivir in HBSS in the absence of any permeability enhancer compounds.

As used herein, the term "fold increase" designates the multiplicative effect on peramivir permeability provided by the enhancer. Thus, the degree of permeability enhancement may be expressed either as a percentage of the permeability of peramivir alone (in the absence of an permeability enhancing compound or in the presence of a compound which is ineffective in enhancing its permeability), in which case a result of 100% or less indicates no enhancement in permeability. Likewise, these values can be (and are in the figures and in the data sets below) reported as a "fold" value in which 1-fold is equivalent to peramivir alone (i.e., the same as 100%), a 1.5-fold value is the same as 150% of the value for peramivir alone, a fold value of 5 is the equivalent of 500% enhancement, and so forth.

Example 2

Evaluation of Various Permeability Enhancers on Caco-2 Permeability of Peramivir As shown in FIG. 1, Caco-2 cell permeability of peramivir was enhanced when combined with a variety of permeability enhancers at a single concentration.

A significant permeability increase was provided by Capmul® MCM L8, with significant increases also observed using many of the Gattefosse compositions. Compared to other materials so far tested, Capmul® MCM L8 seems to have additional advantages. As shown in FIGS. 2 and 3, the permeability enhancement effect by Capmul® MCM L8 (FIG. 2) seems to be saturable and occurs at rather low levels of the enhancer by weight compared to Gattefosse compositions (FIG. 3).

CAPMUL® MCM L8. Caco-2 permeability of peramivir combined with the CAPMUL® MCM L8 was performed as described above. The results are reported in FIG. 2 and Table 1, the former showing a visual representation of the comparative fold increase and related data from one dataset, the latter showing another dataset illustrating both the observed rate of peramivir transport across the membrane (ng peramivir transported/minute) and the fold increase in permeability across the Caco-2 cell membranes due to permeability enhancers, as compared to a control containing peramivir alone, both at a peramivir concentration of 15 μg/mL.

Variation of CAPMUL® MCM L8 concentrations resulted in a significant increase in peramivir permeability across Caco-2 cell membranes as CAPMUL® MCM L8 was increased from 0.5% to 1% in HBSS. In tests performed to date the best permeability enhancement was observed at about 1% CAPMUL® MCM L8 concentration, with slightly suppressed permeability at higher (for example, 5%) concentration. As can be seen, a significant improvement in permeability was obtained by including CAPMUL® MCM L8 as a peramivir permeability enhancer.

GATTEFOSSÉ 61A Through GATTEFOSSÉ 61H.

The results obtained by including GATTEFOSSÉ compositions 61A through 61H at concentrations varying from 0.5% to 2% in an HBSS solution containing 15 μg/mL of peramivir are shown in the Table below. As can be seen, significant increases in peramivir permeability were effected by inclusion of the GATTEFOSSÉ 61A through 61H compounds, generally at or above an enhancer compound concentration of at least 0.5%. Similar results are graphically shown for another Gattefosse dataset illustrating compositions 61A, 61E and 61F in FIG. 3.

Dimethylpalmityl-Ammonio Propanesulfonate. Not all potential permeability enhancers have been shown to be effective for peramivir in Caco-2 cell assays. For example, Tween-80, sodium salicylate, and methylpiperazine have been shown for the most part to be negative. Additional compounds and compositions have been tested to develop an increased understanding of the mechanism or mechanisms that are relevant for peramivir permeability enhancement. Promising new data also involves phosphatidylcholine (PC) and 3-(N,N-dimethylpalmitylammonio)propanesulfonate (PPS). PC has shown some potential for peramivir permeability enhancement in Caco-2 cell assays but its aqueous insolubility confounds the results. PC also appears to act through a tight junction regulatory mechanism.

In contrast to the other permeability enhancing compositions that alter of tight-junction behavior, PPS acts through a different mechanism. PPS is a zwitterionic detergent and has membrane fluidizing properties that enhance transport using transcellular permeability pathway. As shown in FIG. 4, Caco-2 cell assays with PPS varying from 0.001% to 0.01% final concentration provided substantially increased peramivir permeability on par to that seen with Capmul MCM L8. This result is especially interesting in comparison to the negative results with Tween-80, a non-ionic surfactant that was also anticipated to also modify membrane fluidity properties. Additional tests on other non-ionic and ionic surfactants, including bile salts, will be conducted. Although PPS is not listed on the FDA's list of approved inactive ingredients, it is not cytotoxic in the concentrations used. Table 1 also shows the dose-response characteristics of other permeability enhancers according to the invention, on peramivir transport across a Caco-2 cell monolayer. As can be seen, significant permeability enhancement was obtained when 3-(N,N-dimethylpalmitylammonio)propane sulfonate (PPS), Glycerol. The ability of glycerol to enhance peramivir permeability is shown in the Table 1 below. Less than 150% peramivir permeability enhancement was obtained at lower glycerol concentrations at or below about 1%. However, a substantial increase in permeability enhancement was obtained between when the glycerol concentration was above about 1%, suitably in the range from about 2% to as high as 10%.

The results shown in FIG. 5 demonstrate that similar to Capmul MCM L8, glycerol is ineffective in enhancing permeability at low concentrations but provides substantially increased permeability at higher concentrations of up to 5%. This result is consistent with published observations that glycerol disrupts tight junction organization leading to increased paracellular transport (Wiebe J P, Kowalik A, Gallardi R L, Egeler O, and Clubb B H (2000) "Glycerol disrupts tight junction-associated actin microfilaments, occluding, and microtubules in Sertoli cells", J. Androl, 21, 625-635). Both the safety profile of glycerol and its in vivo permeability enhancement capability with peramivir make it an attractive alternative for consideration in human trials Other permeability enhancers. Gelucire 44/14, phosphatidylcholine, Tween 20, and N-methylpiperazine were used as permeability enhancers. With some of these substantial enhancement was obtained at very low enhancer concentration, in some instances as low as 0.0016% (Table 1),

TABLE 1

Effect of varying permeability enhancer concentrations on transport of peramivir across a Caco-2 cell membrane.

| Enhancer | Enhancer Concentration | ng peramivir transported/min | Negative Control ng peramivir transported/min | Fold-Enhancement Over Control |
|---|---|---|---|---|
| Capmul MCM L8 | 0.50% | 9.97 | 0.33 | 30.2 |
|  | 1.00% | 11.07 | 0.33 | 33.6 |
|  | 2.00% | 10.09 | 0.33 | 30.6 |
| Glycerol | 0.50% | 0.16 | 0.14 | 1.14 |
|  | 1% | 0.18 | 0.14 | 1.29 |
|  | 2% | 0.97 | 0.14 | 6.93 |
|  | 5% | 4.35 | 0.14 | 31.1 |
|  | 10% | 5.34 | 0.14 | 38.1 |
| Gattefosse 61A | 0.50% | 1.34 | 0.33 | 4.06 |
|  | 1% | 1.97 | 0.33 | 5.97 |
|  | 2% | 4.41 | 0.33 | 13.4 |
| Gattefosse 61B | 0.50% | 0.96 | 0.33 | 2.91 |
|  | 1% | 1.74 | 0.33 | 5.27 |
|  | 2% | 2.16 | 0.33 | 6.55 |
| Gattefosse 61C | 0.50% | 0.33 | 0.33 | 1 |
|  | 1% | 0.49 | 0.33 | 1.48 |
|  | 2% | 0.87 | 0.33 | 2.64 |
| Gattefosse 61D | 0.50% | 0.68 | 0.33 | 2.06 |
|  | 1% | 0.47 | 0.33 | 1.42 |
|  | 2% | 0.6 | 0.33 | 1.82 |
| Gattefosse 61E | 0.50% | 1.34 | 0.33 | 4.06 |
|  | 1% | 2.02 | 0.33 | 6.12 |
|  | 2% | 4.56 | 0.33 | 13.8 |
| Gattefosse 61F | 0.50% | 1.31 | 0.33 | 3.97 |
|  | 1% | 1.78 | 0.33 | 5.39 |
|  | 2% | 3.3 | 0.33 | 10 |
| Gattefosse 61G | 0.50% | 1.06 | 0.33 | 3.21 |
|  | 1% | 1.52 | 0.33 | 4.61 |
|  | 2% | 1.12 | 0.33 | 3.39 |
| Gattefosse 61H | 0.50% | 1.06 | 0.33 | 3.21 |
|  | 1% | 2.42 | 0.33 | 7.33 |
|  | 2% | 5.81 | 0.33 | 17.6 |
| PPS | 0.001% | 0.48 | 0.18 | 2.67 |
|  | 0.005% | 1.97 | 0.18 | 10.9 |
|  | 0.010% | 3.73 | 0.18 | 20.7 |
| TPGS | 1% | 9.52 | 0.33 | 28.9 |
| Capmul MCM L8 + TPGS | 1% | 14.35 | 0.33 | 43.5 |
| Leucine | 0.0024% | 2.2 | 0.57 | 3.86 |
| Alanine | 0.0016% | 2.5 | 0.57 | 4.39 |
| Gelucire 44/14 | 0.50% | 0.75 | 0.33 | 2.27 |
|  | 1% | 2.06 | 0.33 | 6.24 |
|  | 2% | 2.6 | 0.33 | 7.9 |
| Phosphatidylcholine | 0.05% | 0.4 | 0.19 | 2.11 |
|  | 0.10% | 0.4 | 0.19 | 2.11 |
|  | 0.20% | 1.33 | 0.19 | 7 |
| Tween 20 | 0.50% | 1.96 | 0.33 | 5.94 |
|  | 1% | 3.12 | 0.33 | 9.45 |
|  | 2% | 3.18 | 0.33 | 9.64 |
| N-Methylpiperazine | 0.50% | 0.39 | 0.33 | 1.18 |
|  | 1% | 0.85 | 0.33 | 2.58 |
|  | 2% | 0.75 | 0.33 | 2.27 |

Example 3

Proposed Initial Human Pharmacokinetic Trial

This is a prophetic example. To be effective, a proposed enteric-coated peramivir oral dosage form should contain an adequate amount of a permeability enhancer to impact either the paracellular or transcellular transport pathways, or both. Once such a condition has been identified, the amount of peramivir can be appropriately scaled to achieve the desired blood level. For example, the amount of permeability enhancer should take into account the volume of a human duodenum: to 750-1000 mg and 1500-2000 mg of enhancer should roughly correspond to the dose at the lower and upper ranges, respectively, of the proportionate volume of the human duodenum.

An initial human PK trial should be designed to test the utility of both Capmul® MCM L8 and glycerol. A four- or five-way crossover protocol utilizing enteric-coated softgels is envisioned. This involves dosing subjects with either one or two softgels in separate arms and examining the PK data to determine if the peramivir blood levels are dose proportional. Peramivir dose proportionality would indicate a near saturating effect from the lower dose of the permeability enhancer used. Alternatively, separate dosage forms can be manufactured for each arm wherein peramivir is kept constant and two amounts of permeability enhancer is used. The following arms are proposed to both test permeability enhancer function and to limit the number of dosage forms that must be manufactured.

Arm 1: 150 mg peramivir, 765 mg Capmul MCM L8 in a single dosage form (765 mg of Capmul MCM L8 is the highest currently approved amount on the FDA inactive ingredient list.)

Arm 2: 300 mg peramivir, 1530 mg Capmul MCM L8 dosed as two gelcaps used in Arm 1.

Arm 3: 150 mg peramivir, 1000 mg glycerol in a single dosage form (although 223.8 mg of glycerol is the highest currently approved amount, its safety and use as a food additive should not present a significant regulatory barrier for increasing that limit.)

Arm 4: 300 mg peramivir, 2000 mg glycerol dosed as two gelcaps used in Arm 3.

Arm 5: 150 mg or 300 mg peramivir plus inert filler in a single dosage form (this is an optional negative control arm included to scale the impact of the permeability enhancers. It may be unnecessary depending on prior clinical experience with oral peramivir.)

It is anticipated that results from this trial will provide important information to demonstrate the potential to deliver peramivir orally and to use as a guide in defining an optimized formulation and peramivir drug load.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. An oral dosage form comprising a composition having an enteric- or pH-sensitive coating or layer surrounding same, said composition comprising:
   a neuraminidase inhibitor having a guanidino group thereon, and
   a permeability enhancer comprising glycerol,
   wherein the amount of the neuraminidase inhibitor transported across a Caco-2 cell membrane by said oral dosage form is increased by at least 150% relative to the amount transported across the Caco-2 Cell membrane in the absence of the permeability enhancer.

2. The oral dosage form of claim 1, wherein the permeability enhancer further comprises one or more agent selected from the group consisting of fatty acids, fatty acid esters, fatty acid salts, surfactants, cyclodextrins, sodium salicylate, ethylenediamine tetraacetic acid, citric acid, chitosan, chitosan derivatives, N-trimethyl chitosan chloride, monocarboxymethyl-chitosan, palmitoyl carnitine chloride, acyl carnitines, ethylene glycol tetraacetic acid, 3-alkylamido-2-alkoxypropyl-phosphocholine derivatives, alkanoylcholines, N-acetylated amino acids, mucoadhesive polymers, phospholipids, piperine, 1-methylpiperazine, α-amino acids, and mineral oil.

3. The oral dosage form of claim 1, wherein the permeability enhancer further comprises one or more agent selected from the group consisting of one or more fatty acid esters, monoglycerides of capric and/or caprylic acid, diglycerides of capric and/or caprylic acid, and dimethylpalmityl-ammonio propanesulfonate.

4. The oral dosage form of claim 1, wherein the neuraminidase inhibitor is selected from the group consisting of oseltamivir, zanamivir and peramivir.

5. The oral dosage form of claim 1, wherein the neuraminidase inhibitor and the permeability enhancer form a mixture that is emulsified.

6. The oral dosage form of claim 1, wherein the composition comprises a therapeutically effective amount of the neuraminidase inhibitor and a permeability-enhancing amount of a permeability enhancer.

7. The oral dosage form of claim 6, wherein the permeability enhancer further comprises one or more agent selected from the group consisting of monoglycerides of capric and/or caprylic acid, diglycerides of capric and/or caprylic acid, and dimethylpalmityl-ammonio propanesulfonate.

8. The oral dosage form of claim 6, wherein the permeability enhancer is present in the composition at a concentration from about 5% to about 95% of the combined weight of the neuraminidase inhibitor and the permeability enhancer.

9. A method of treating or preventing influenza infection, comprising administering to a subject in need thereof the oral dosage form of claim 1.

10. A method of treating or preventing influenza infection, comprising administering to a subject in need thereof the oral dosage form of claim 6.

11. The method of claim 10, wherein the permeability enhancer further comprises one or more agent selected from the group consisting of monoglycerides of capric and/or caprylic acid, diglycerides of capric and/or caprylic acid, and dimethylpalmityl-ammonio propanesulfonate.

12. The method of claim 10, wherein the neuraminidase inhibitor is selected from the group consisting of oseltamivir, zanamivir and peramivir.

13. The oral dosage form of claim 6, wherein the oral dosage form is an encapsulated gel comprising an outer gel cap containing the composition.

14. The oral dosage form of claim 6, wherein the neuraminidase inhibitor and permeability enhancer are mixed by sonication.

15. A method for improving the oral bioavailability of a neuraminidase inhibitor having a guanidino group thereon, that is not absorbed or is only weakly absorbed through a cell membrane to a subject in need thereof, said method comprising orally administering to said subject an oral dosage form of claim 1.

\* \* \* \* \*

UNITED STATES PATENT AND TRADEMARK OFFICE
CERTIFICATE OF CORRECTION

| | |
|---|---|
| PATENT NO. | : 8,609,139 B2 |
| APPLICATION NO. | : 12/741141 |
| DATED | : December 17, 2013 |
| INVENTOR(S) | : Holmes et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 456 days.

Signed and Sealed this
Twenty-first Day of July, 2015

Michelle K. Lee
*Director of the United States Patent and Trademark Office*